United States Patent
Pirogov et al.

(10) Patent No.: US 12,083,361 B2
(45) Date of Patent: Sep. 10, 2024

(54) SYSTEMS, DEVICES, AND METHODS FOR UNIFIED MODULAR BEAM DIAGNOSTICS

(71) Applicant: TAE TECHNOLOGIES, INC., Foothill Ranch, CA (US)

(72) Inventors: Konstantin Pirogov, Foothill Ranch, CA (US); Andrey A. Korepanov, Foothill Ranch, CA (US); Alexander Dunaevsky, Corona, CA (US)

(73) Assignee: TAE TECHNOLOGIES, INC., Foothill Ranch, CA (US)

( * ) Notice: Subject to any disclaimer, the term of this patent is extended or adjusted under 35 U.S.C. 154(b) by 0 days.

(21) Appl. No.: 17/411,832

(22) Filed: Aug. 25, 2021

(65) Prior Publication Data

US 2022/0062657 A1    Mar. 3, 2022

Related U.S. Application Data

(60) Provisional application No. 63/070,702, filed on Aug. 26, 2020.

(51) Int. Cl.
*A61N 5/10* (2006.01)
*G01T 1/29* (2006.01)
*G21K 5/00* (2006.01)

(52) U.S. Cl.
CPC ......... *A61N 5/1048* (2013.01); *A61N 5/1067* (2013.01); *A61N 5/1075* (2013.01); *A61N 5/1078* (2013.01); *G01T 1/29* (2013.01); *G21K 5/00* (2013.01); *A61N 2005/1074* (2013.01); *A61N 2005/1087* (2013.01); *A61N 2005/1089* (2013.01); *A61N 2005/109* (2013.01)

(58) Field of Classification Search
CPC ...... A61N 5/10; A61N 5/1048; A61N 5/1049; A61N 5/1064; A61N 5/1065; A61N 5/1067; A61N 5/1071; A61N 2005/1074; A61N 5/1075; A61N 5/1077; A61N 5/1078; A61N 5/1079; A61N 2005/1085; A61N 2005/1087; A61N 2005/1089; A61N 2005/109
USPC .......................................................... 378/65
See application file for complete search history.

(56) References Cited

U.S. PATENT DOCUMENTS

| | | | |
|---|---|---|---|
| 6,941,400 B2 * | 9/2005 | Hungerbuehler | G06F 1/12 710/301 |
| 7,542,867 B2 * | 6/2009 | Steger | G01D 9/005 717/124 |

(Continued)

FOREIGN PATENT DOCUMENTS

JP    2008186682 A    8/2008

OTHER PUBLICATIONS

IBM Power Systems, Rack, rack features, and installing systems or expansion units into a rack (2007). (Year: 2007).*

(Continued)

*Primary Examiner* — Allen C. Ho
(74) *Attorney, Agent, or Firm* — ALSTON & BIRD LLP

(57) ABSTRACT

Embodiments of systems, devices, and methods relate to a modular diagnostics interface system. An example modular diagnostics interface system includes one or more insertable measurement boards configured to communicably couple with a backplane of a modular measurement rack, and configured to collect a measured current from a component of a beamline.

26 Claims, 9 Drawing Sheets

(56) References Cited

U.S. PATENT DOCUMENTS

| | | | | |
|---|---|---|---|---|
| 7,685,349 B2* | 3/2010 | Allen | | H04Q 1/08 |
| | | | | 710/301 |
| 7,865,326 B2* | 1/2011 | Johnson | | G01D 11/24 |
| | | | | 710/301 |
| 8,755,165 B2* | 6/2014 | Hansen | | H02H 3/247 |
| | | | | 361/235 |
| 9,870,333 B1* | 1/2018 | Lam | | G06F 13/385 |
| 10,095,594 B2* | 10/2018 | Vanderah | | G06F 13/364 |
| 10,352,972 B1* | 7/2019 | Nayak | | G08B 5/36 |
| 10,360,125 B2* | 7/2019 | Vanderah | | G06F 13/4068 |
| 10,849,697 B2* | 12/2020 | Yates | | A61B 34/35 |
| 11,076,921 B2* | 8/2021 | Shelton, IV | | G16H 40/40 |
| 11,179,208 B2* | 11/2021 | Yates | | G16H 40/20 |
| 11,202,570 B2* | 12/2021 | Shelton, IV | | A61B 90/37 |
| 11,213,359 B2* | 1/2022 | Shelton, IV | | A61B 34/76 |
| 11,218,822 B2* | 1/2022 | Morgan | | H04R 1/22 |
| 11,291,495 B2* | 4/2022 | Yates | | A61B 18/1445 |
| 11,350,978 B2* | 6/2022 | Henderson | | A61B 50/13 |
| 11,410,259 B2* | 8/2022 | Harris | | G06Q 10/10 |
| 11,419,630 B2* | 8/2022 | Yates | | A61B 17/3211 |
| 11,432,885 B2* | 9/2022 | Shelton, IV | | A61B 34/35 |
| 11,471,206 B2* | 10/2022 | Henderson | | A61B 18/16 |
| 11,678,925 B2* | 6/2023 | Henderson | | A61B 18/16 |
| | | | | 606/34 |
| 2008/0310113 A1 | 12/2008 | Renders et al. | | |

OTHER PUBLICATIONS

WIPO Application No. PCT/US2021/047603, PCT International Search Report and Written Opinion of the International Searching Authority mailed Jan. 4, 2022.

WIPO Application No. PCT/US2021/047603, International Preliminary Report on Patentability mailed Feb. 18, 2023.

* cited by examiner

SYSTEMS, DEVICES, AND METHODS FOR UNIFIED MODULAR BEAM DIAGNOSTICS

CROSS-REFERENCE TO RELATED APPLICATIONS

The present application claims priority to U.S. Provisional Application Ser. No. 63/070,702, titled "SYSTEMS, DEVICES, AND METHODS FOR UNIFIED MODULAR BEAM DIAGNOSTICS," filed Aug. 26, 2020, the contents of which are incorporated herein by reference in their entirety for all purposes.

FIELD

The subject matter described herein relates generally to beam systems and, in particular, to beam diagnostics of a beamline of the beam system. The subject matter further relates to systems and methods for facilitating unified modular beam diagnostics.

BACKGROUND

Boron neutron capture therapy (BNCT) is a modality of treatment of a variety of types of cancer, including some of the most difficult types. BNCT is a technique that selectively aims to treat tumor cells while sparing the normal cells using a boron compound. A substance that contains boron is injected into a blood vessel, and the boron collects in tumor cells. The patient then receives radiation therapy with neutrons (e.g., in the form of a neutron beam). The neutrons react with the boron to kill the tumor cells without harming normal cells. Prolonged clinical research has proven that a beam of neutrons with an energy spectrum within 3-30 kiloelectronvolts (keV) can be preferable to achieve a more efficient cancer treatment while decreasing a radiation load on a patient. This energy spectrum or range is frequently referred to as epithermal.

Most conventional methods for the generation of epithermal neutrons (e.g., epithermal neutron beams) are based on nuclear reactions of protons (e.g., a proton beam) with either beryllium or lithium (e.g., a beryllium target or a lithium target).

For accelerator based solutions, beam diagnostics is an intrinsic part of the charged particle beamline design. The deliverables of such beam diagnostics include providing information about beam parameters and characteristics which are extensively use for arrangement and control of beamline elements, beam shaping, beam focusing, beam bending, cleaning and rotation or beamline elements, beam monitoring and statistics, and more.

Conventionally available diagnostic tools are supplied with their own measuring systems (e.g., a UniBEaM75 XY beam profiler from D-Pace, Inc.). However, biasing power supplies necessary for such dedicated measuring systems are bulky, expensive, and not fully suitable for measurements of small currents in a wide frequency range. In a pulsed mode of a beam system, systems require additional circuits to synchronize data acquisition with the beam current pulse.

For these and other reasons, a need exists for improved, efficient, and compact systems, devices, and methods that provide unified beam diagnostics within a beam system.

SUMMARY

Embodiments of systems, devices, and methods relate to accelerator based beam systems and, more particularly, systems, devices, and methods for facilitating unified modular beam diagnostics. Example embodiments of a modular diagnostics interface system can include one or more insertable modules configured to communicably couple with a backplane of a modular measurement rack, and configured to perform various functions (e.g., diagnostics, communication, power supply) with respect to a beam system.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, can be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes can be illustrated schematically rather than literally or precisely.

DETAILED DESCRIPTION

Figure 1A:
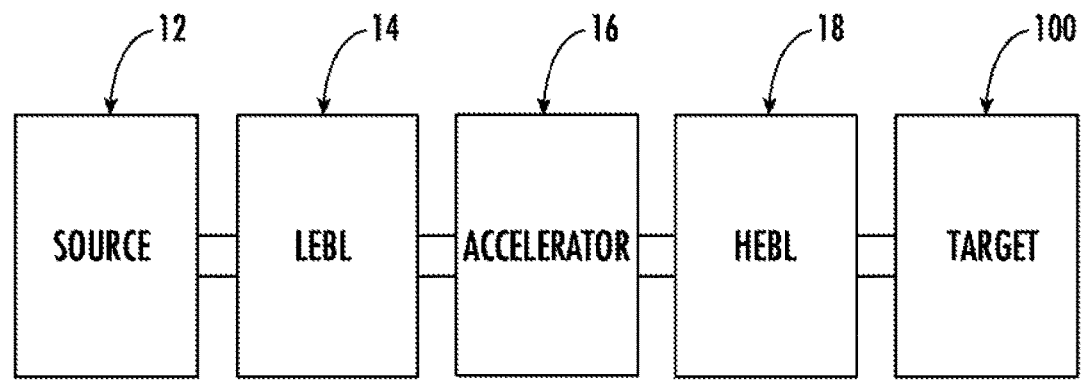
FIG. 1A is a schematic diagram of an example embodiment of a neutron beam system for use with embodiments of the present disclosure.

Before the present subject matter is described in detail, it is to be understood that this disclosure is not limited to the particular embodiments described, as such can, of course, vary. It is also to be understood that the terminology used herein is for the purpose of describing particular embodiments only, and is not intended to be limiting, since the scope of the present disclosure will be limited only by the appended claims.

The term "particle" is used broadly herein and, unless otherwise limited, can be used to describe an electron, a proton (or H+ ion), or a neutral, as well as a species having more than one electron, proton, and/or neutron (e.g., other ions, atoms, and molecules).

Example embodiments of systems, devices, and methods are described herein for diagnostics in a beam system (e.g., including a particle accelerator). The embodiments described herein can be used with any type of particle accelerator or in any particle accelerator application involving production of a charged particle beam at specified energies for supply to the particle accelerator. Embodiments herein can be used in numerous applications, an example of which is as a neutron beam system for generation of a neutron beam for use in boron neutron capture therapy (BNCT). For ease of description, many embodiments described herein will be done so in the context of a neutron beam system for use in BNCT, although the embodiments are not limited to just the generation of neutron beams nor BNCT applications in particular.

Example embodiments of systems, devices, and methods are described herein for facilitating unified beam diagnostics. Beam diagnostics in accelerators, such as those with direct current (DC) beams, include tools capable of measuring beam parameters via electrodes immersed in the area of the beam system occupied by the beam or its periphery. These electrodes, varying by shape and function, share a common feature: they collect charged particles by applying a certain bias to the electrode, and measure the collected current. Examples of tools employing the electrodes for measuring beam parameters can include apertures, grids, faraday cups, beam position monitors, beam profilers (e.g., wire scanning beam profilers), and the like.

Use of the above described and other tools involves biasing of electrodes and measuring current of the electrodes. In example embodiments, a biasing power supply for use with these tools operates in a multi-quadrant regime (e.g., is able to provide positive and negative bias voltage and is able to source and sink current). The measured current can be transferred to a digital acquisition system (DAQ) with adequate galvanic isolation to prevent ground loops. Current measurement circuits can include electromagnetic interference (EMI) protection from an accelerator exposed side (that is, a side of the current measurement circuits facing toward an accelerator of the beam system). In embodiments, the example unified diagnostics system has sufficient frequency bandwidth to manifest a response time suitable for when the beam system operates with a DC beam or a pulsed beam.

FIG. 1A is a schematic diagram of an example embodiment of a beam system 10 for use with embodiments of the present disclosure. Here, the beam system 10 includes a source 12, a low-energy beamline (LEBL) 14, an accelerator 16 coupled to the low-energy beamline (LEBL) 14, and a high-energy beamline (HEBL) 18 extending from the accelerator 16 to a target 100. LEBL 14 is configured to transport a beam from source 12 to an input of accelerator 16, which in turn is configured to produce a beam by accelerating the beam transported by LEBL 14. HEBL 18 transfers the beam from an output of accelerator 16 to target 100. Target 100 can be a structure configured to produce a desired result in response to the stimulus applied by the incident beam, or can modify the nature of the beam. Target 100 can be a component of the beam system 10 or can be a workpiece that is conditioned or manufactured, at least in part, by the beam system 10.

Figure 1B:
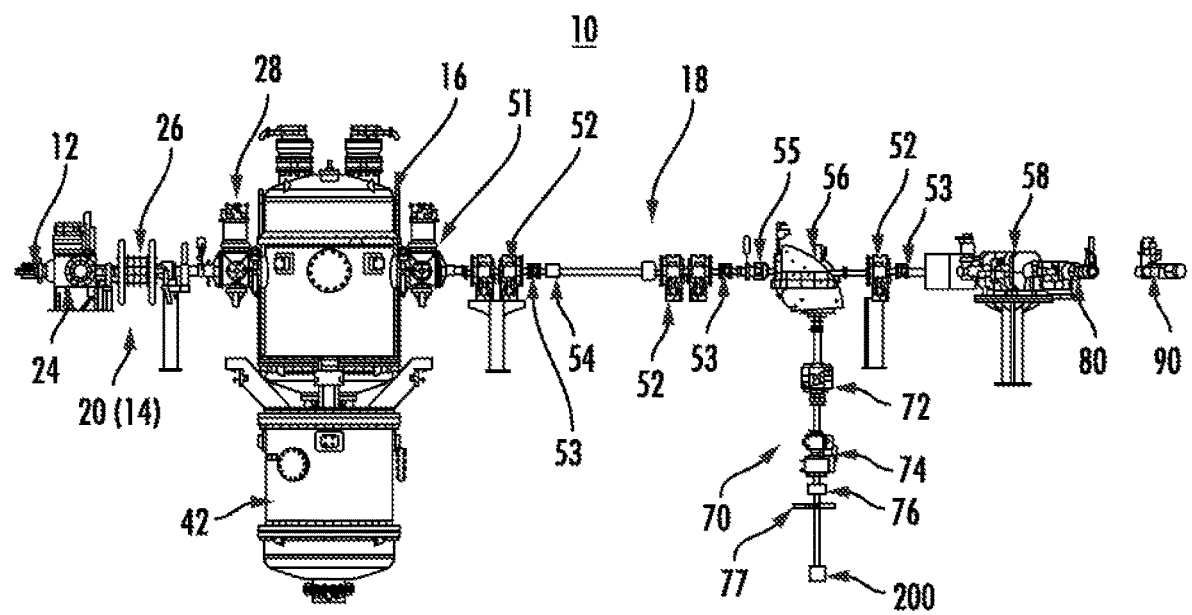
FIG. 1B is a schematic diagram of an example embodiment of a neutron beam system for use in boron neutron capture therapy (BNCT).

FIG. 1B is a schematic diagram illustrating another example embodiment of a neutron beam system 10 for use in boron neutron capture therapy (BNCT). Here, source 12 is an ion source and accelerator 16 is a tandem accelerator. Neutron beam system 10 includes a pre-accelerator system 20, serving as a charged particle beam injector, high voltage (HV) tandem accelerator 16 coupled to pre-accelerator system 20, and HEBL 18 extending from tandem accelerator 16 to a neutron target assembly 200 housing target 100 (not shown). In this embodiment target 100 is configured to generate neutrons in response to impact by protons of a sufficient energy, and can be referred to as a neutron generation target. Neutron beam system 10 as well as pre-accelerator system 20 can also be used for other applications such as those other examples described herein, and is not limited to BNCT.

Pre-accelerator system 20 is configured to transport the ion beam from ion source 12 to the input (e.g., an input aperture) of tandem accelerator 16, and thus also acts as LEBL 14. Tandem accelerator 16, which is powered by a high voltage power supply 42 coupled thereto, can produce a proton beam with an energy generally equal to twice the voltage applied to the accelerating electrodes positioned within accelerator 16. The energy level of the proton beam can be achieved by accelerating the beam of negative hydrogen ions from the input of accelerator 16 to the innermost high-potential electrode, stripping two electrons from each ion, and then accelerating the resulting protons downstream by the same applied voltage.

HEBL 18 can transfer the proton beam from the output of accelerator 16 to the target within neutron target assembly 200 positioned at the end of a branch 70 of the beamline extending into a patient treatment room. System 10 can be configured to direct the proton beam to any number of one or more targets and associated treatment areas. In this embodiment, the HEBL 18 includes three branches 70, 80 and 90 that can extend into three different patient treatment rooms, where each branch can terminate in a target assembly 200 and downstream beam shaping apparatus (not shown). HEBL 18 can include a pump chamber 51, quadrupole magnets 52 and 72 to prevent de-focusing of the beam, dipole or bending magnets 56 and 58 to steer the beam into treatment rooms, beam correctors 53, diagnostics such as current monitors 54 and 76, a fast beam position monitor 55 section, and a scanning magnet 74.

The design of HEBL 18 depends on the configuration of the treatment facility (e.g., a single-story configuration of a treatment facility, a two-story configuration of a treatment facility, and the like). The beam can be delivered to target assembly (e.g., positioned near a treatment room) 200 with the use of bending magnet 56. Quadrupole magnets 72 can be included to then focus the beam to a certain size at the target. Then, the beam passes one or more scanning magnets 74, which provides lateral movement of the beam onto the target surface in a desired pattern (e.g., spiral, curved, stepped in rows and columns, combinations thereof, and others). The beam lateral movement can help achieve smooth and even time-averaged distribution of the proton beam on the lithium target, preventing overheating and making the neutron generation as uniform as possible within the lithium layer.

After entering scanning magnets 74, the beam can be delivered into a current monitor 76, which measures beam current. Target assembly 200 can be physically separated from the HEBL volume with a gate valve 77. The main function of the gate valve is separation of the vacuum volume of the beamline from the target while loading the target and/or exchanging a used target for a new one. In embodiments, the beam may not be bent by 90 degrees by a bending magnet 56, it rather goes straight to the right of FIG. 1B, then enters quadrupole magnets 52, which are located in the horizontal beamline. The beam could be subsequently bent by another bending magnet 58 to a needed angle, depending on the building and room configuration. Otherwise, bending magnet 58 could be replaced with a Y-shaped magnet in order to split the beamline into two directions for two different treatment rooms located on the same floor.

In example embodiments, one or more beam dumps can be placed along the beam system. A beam dump, for example, can be placed in a position such that if any of bending magnet 56 or quadrupole magnets 52 are disabled, moved, or not functioning properly, the beam passing beyond the magnets can be fully and safely collected by the one or more beam dumps. Current measured at the one or more beam dumps can be utilized by a control system or a user using a computing device to understand beam and/or adjust beam parameters.

Figure 2:
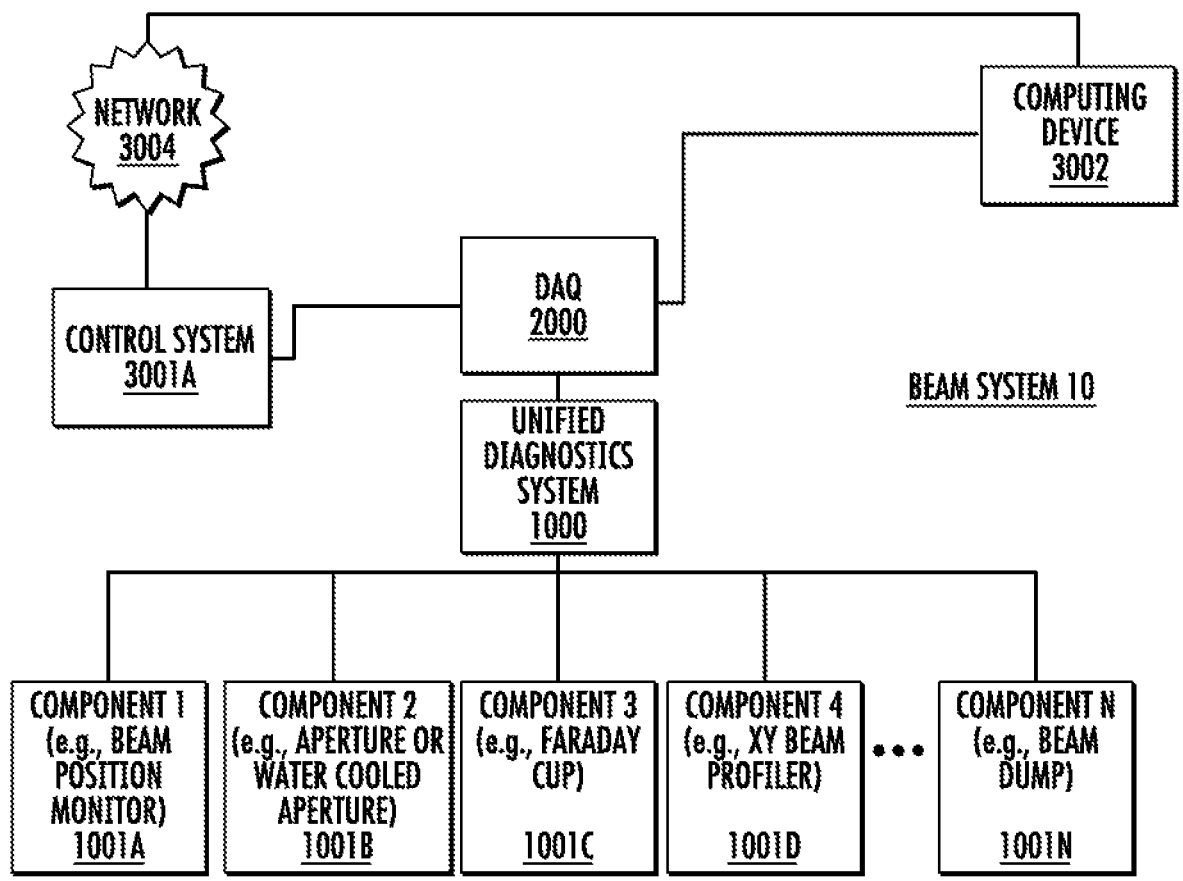
FIG. 2 is a block diagram depicting an example embodiment of a system within which an example embodiment of a unified diagnostics system operates.

FIG. 2 is a block diagram depicting an example embodiment of a beam system 10 within which an example embodiment of a unified modular diagnostics system 1000 operates. Beam system 10 can also include one or more computing devices 3002, one or more digital acquisition systems (DAQ) 2000, and one or more control systems 3001A. Beam system 10 can be a neutron beam system as described herein, or configured otherwise. Control system 3001A can communicate with computing device 3002 in order to interact with the systems and components of beam system 10. Each of these devices and/or systems are configured to communicate directly with one another or via a local network, such as network 3004. Beam system 10 employs unified diagnostics system 1000 to perform various functions with respect to the beam system, such as diagnostics, communication, power supply of diagnostics components, and the like. For example, one diagnostics function can be collection of current measurements from one or more beam system components (e.g., Component 1 1001A, Component 2 1001B, Component 3 1001C, Component 4 1001D, . . . Component N 1001N). The measurements can then be provided to DAQ 2000 (or another device) which, in turn, can provide one or more such measurements to control system 3001A and/or computing device 3002. In some embodiments the DAQ can be integrated as part of system 1000.

Computing device 3002 can be embodied by one or more various user devices, systems, computing apparatuses, and the like. For example, a first computing device 3002 can be a desktop computer associated with a particular user, while another computing device 3002 can be a laptop computer associated with a particular user, and yet another computing device 3002 can be a mobile device (e.g., a tablet or smart device). Each of computing devices 3002 can be configured to communicate with beam system 10, for example through a user interface accessible via the computing device. For example, a user can execute a desktop application on computing device 3002, which is configured to communicate with beam system 10. By using computing device 3002 to communicate with beam system 10, a user can provide operating parameters for beam system 10 (e.g., operating voltages, and the like) according to embodiments described herein. In embodiments, control system 3001A can be configured to receive and apply operating parameters from computing device 3002.

Control system 3001A can be configured to receive measurements, signals, or other data from components of beam system 10. For example, control system 3001A can receive signals of measured current from a beam position monitor (e.g., indicating that a beam passing through components of the beam line is on or off a desired axis), a water-cooled aperture, a faraday cup, an XY beam profiler, a beam dump, and the like. Some components from which the control system 3001A receives signals, by way of digital acquisition system 2000 or other electronic device, can be used during normal operation of system 10 and/or during a calibration or testing operation of system 10. Control system 3001A, depending on the received signals, can provide adjustments to inputs of one or more beam line components, to alter the position or other parameters of the beam. Control system 3001A can also provide information collected from any of the components of beam system 10, including DAQ 2000, to computing device 3002 either directly or via communications network 3004.

Communications network 3004 can include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communications network 3004 can include an 802.11, 802.16, 802.20, and/or WiMax network. Further, the communications network 3004 can include a public network, such as the Internet, a private network, such as an intranet, or combinations thereof, and can utilize a variety of networking protocols now available or later developed including, but not limited to TCP/IP based networking protocols.

Figure 3:
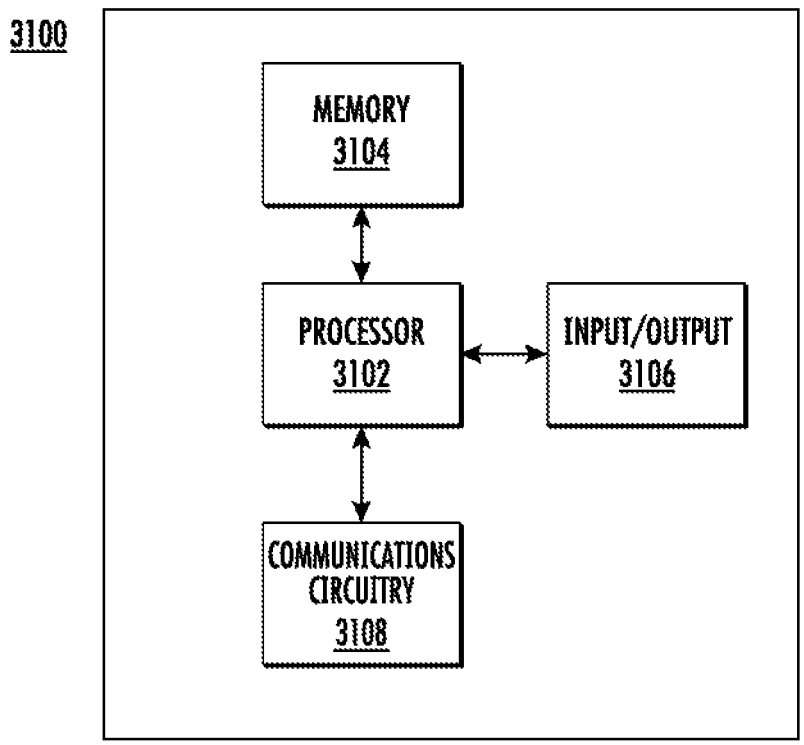
FIG. 3 is a block diagram depicting an example embodiment of a computing apparatus that can be used with embodiments of the present disclosure.

FIG. 3 is a block diagram depicting an example embodiment of an apparatus 3100 that can be used to embody computing device 3002 and/or control system 3001A. Apparatus 3100 can include a processor 3102, a memory 3104, input and/or output device or circuitry 3106, and communications device or circuitry 3108. Each of these components can be communicatively coupled to exchange information with each and every other component. One or more of components 3102-3108 can include similar hardware, or can share the same hardware. For example, two components can both leverage use of the same processor, network interface, storage medium, or the like to perform their associated functions, such that duplicate hardware is not required for each device.

The terms "device" and/or "circuitry" as used herein with respect to components of the apparatus therefore can encompass particular hardware configured with software to perform the functions associated with that particular device, as described herein. These terms should be understood broadly to include hardware, and in some embodiments, software for configuring the hardware. For example, in some embodiments, "device" and/or "circuitry" can include processing circuitry, storage media, network interfaces, input/output devices, and the like. In some embodiments, other elements of apparatus 3100 can provide or supplement the functionality of particular device(s). For example, processor 3102 can provide processing functionality, memory 3104 can provide storage functionality, communications device or circuitry 3108 can provide network interface functionality, and the like.

In some embodiments, processor 3102 (and/or co-processor or any other processing circuitry assisting or otherwise associated with the processor) can be in communication with memory 3104 via a bus for passing information among components of the apparatus. Memory 3104 can be non-transitory and can include, for example, one or more volatile and/or non-volatile memories. In other words, for example, the memory can be an electronic storage device (e.g., a computer readable storage medium.) Memory 3104 can be configured to store information, data, content, applications, instructions, or the like, for enabling the apparatus to carry out various functions in accordance with example embodiments of the present disclosure.

Processor 3102 can be embodied in a number of different ways and can, for example, include one or more processing devices configured to perform independently. Additionally or alternatively, the processor can include one or more processors configured in tandem via a bus to enable independent execution of instructions, pipelining, and/or multi-threading. The use of the terms "processing device" and/or "processing circuitry" can be understood to include a single core processor, a multi-core processor, multiple processors internal to the apparatus, and/or remote or "cloud" processors.

In an example embodiment, processor 3102 can be configured to execute instructions stored in memory 3104 or otherwise accessible to the processor. Alternatively or additionally, the processor can be configured to execute hard-coded functionality. As such, whether configured by hardware or software methods, or by a combination of hardware with software, the processor can represent an entity (e.g., physically embodied in circuitry) capable of performing operations according to an embodiment of the present disclosure while configured accordingly. Alternatively, as another example, when the processor is embodied as an executor of software instructions, the instructions can specifically configure the processor to perform the algorithms and/or operations described herein when the instructions are executed.

In some embodiments, apparatus 3100 can include input/output device 3106 that can, in turn, be in communication with processor 3102 to provide output to the user and, in some embodiments, to receive input from the user. Input/output device 3106 can include a user interface and can include a device display, such as a user device display, that can include a web user interface, a mobile application, a client device, or the like. In some embodiments, input/output device 3106 can also include a keyboard, a mouse, a joystick, a touch screen, touch areas, soft keys, a microphone, a speaker, or other input/output mechanisms. The processor and/or user interface circuitry including the processor can be configured to control one or more functions of one or more user interface elements through computer program instructions (e.g., software and/or firmware) stored on a memory accessible to the processor (e.g., memory 3104, and/or the like).

Communications device or circuitry 3108 can be embodied in either hardware or a combination of hardware and software that is configured to receive and/or transmit data from/to a network and/or any other device or circuitry in communication with apparatus 3100. In this regard, communications device or circuitry 3108 can include, for example, a network interface for enabling communications with a wired or wireless communication network. For example, communications device or circuitry 3108 can include one or more network interface cards, antennas, buses, switches, routers, modems, and supporting hardware and/or software, or any other device suitable for enabling communications via a network. Additionally or alternatively, the communication interface can include the circuitry for interacting with the antenna(s) to cause transmission of signals via the antenna(s) or to handle receipt of signals received via the antenna(s). These signals can be transmitted by apparatus 3100 using any of a number of wireless personal area network (PAN) technologies, such as current and future Bluetooth standards (including Bluetooth and Bluetooth Low Energy (BLE)), infrared wireless (e.g., IrDA), FREC, ultra-wideband (UWB), induction wireless transmission, or the like. In addition, it should be understood that these signals can be transmitted using Wi-Fi, Near Field Communications (NFC), Worldwide Interoperability for Microwave Access (WiMAX), or other proximity-based communications protocols.

Figure 4A:
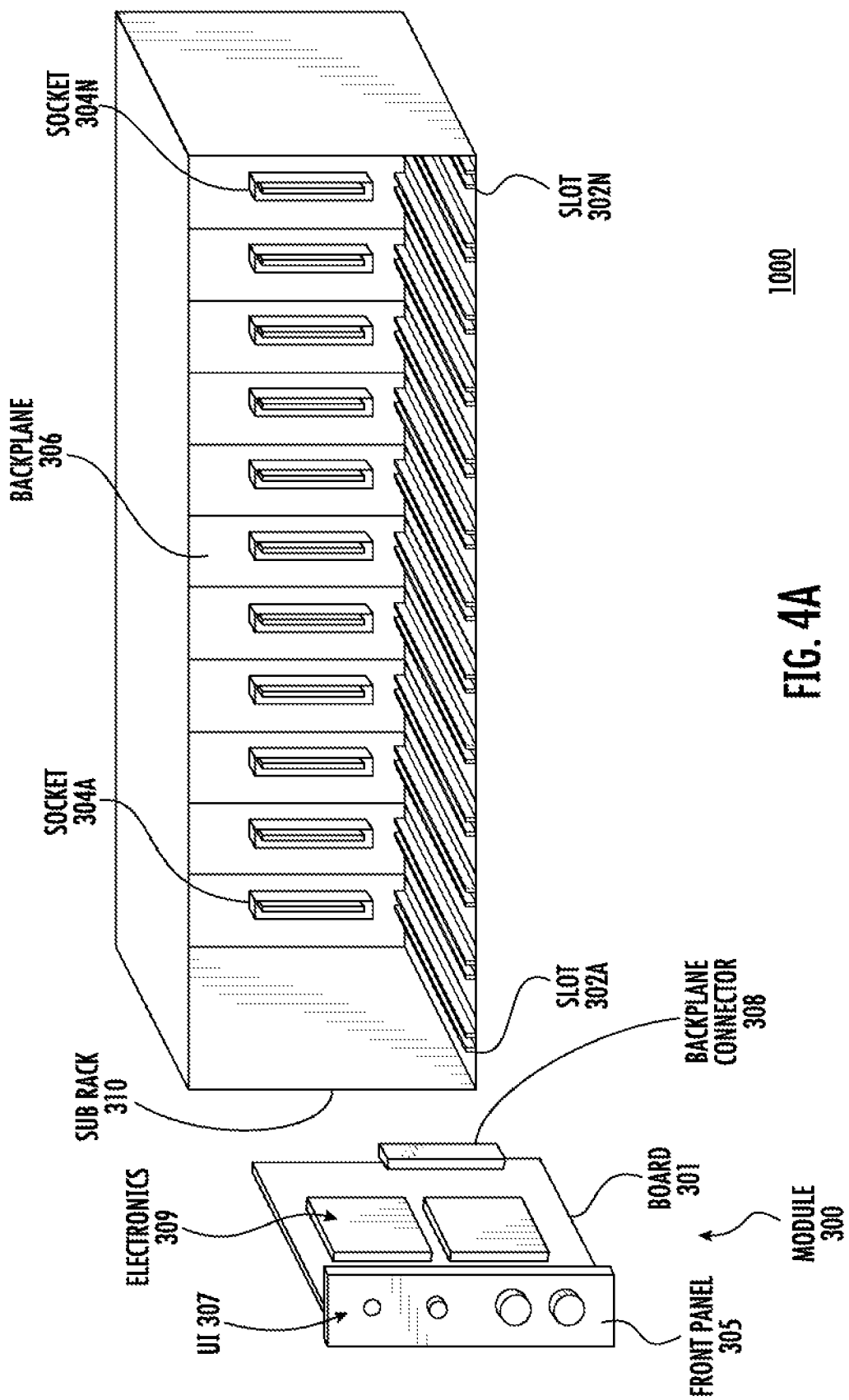
FIG. 4A illustrates an example embodiment of a unified diagnostics sub rack in accordance with various embodiments of the present disclosure.

System 1000 can be configured with multiple diagnostics devices for the various components 1001 arranged together in a modular fashion. FIG. 4A is a perspective view depicting system 1000 in accordance with various example embodiments of the present disclosure. System 1000 includes a unified diagnostics rack 310 that can include one or more slots 302A-302N each configured to receive a module or modular device or card 300, which can have various diagnostics, communication, power supply, and/or other functions. Rack 310 can be a stand-alone rack or can be a sub rack configured to insert into or otherwise act as a shelf of a multi-shelf rack. For convenience rack 310 is referred to herein as a sub rack 310.

Figure 4B:
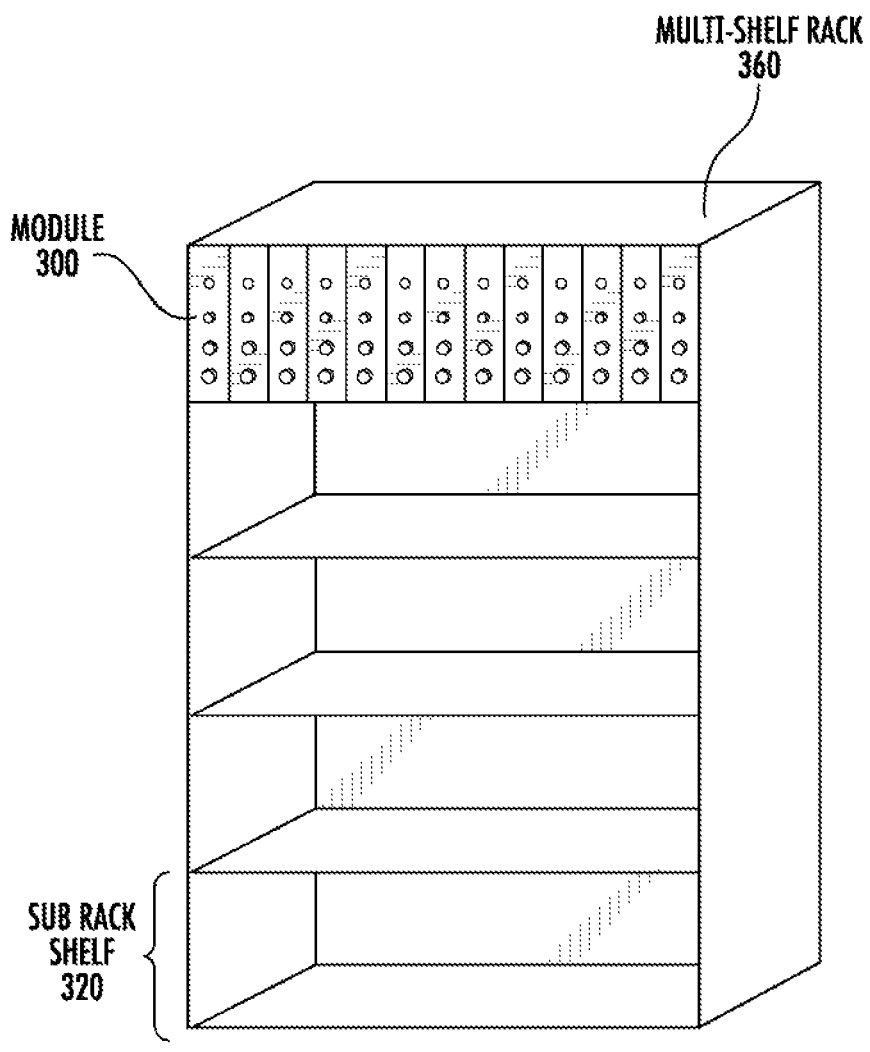
FIG. 4B illustrates an example embodiment of a unified diagnostics rack in accordance with various embodiments of the present disclosure.

FIG. 4B illustrates an example embodiment of a multi-shelf rack 360 in accordance with various embodiments of the present disclosure. Multi-shelf rack 360 can include multiple shelves 320 each configured for housing or coupling to a sub rack 310 (e.g., as shown in FIG. 4A). Rack 360 can house multiple sub racks 310, each housing multiple modules 300. Rack 360 and sub racks 310 can be configured to provide data and information (e.g., measurements) from modules 300 of each sub rack 310 to DAQ 2000 (FIG. 2). Rack 360 can also receive data and information (e.g., instructions to bias) from DAQ 2000 and/or control system 3001A.

Figure 4C:
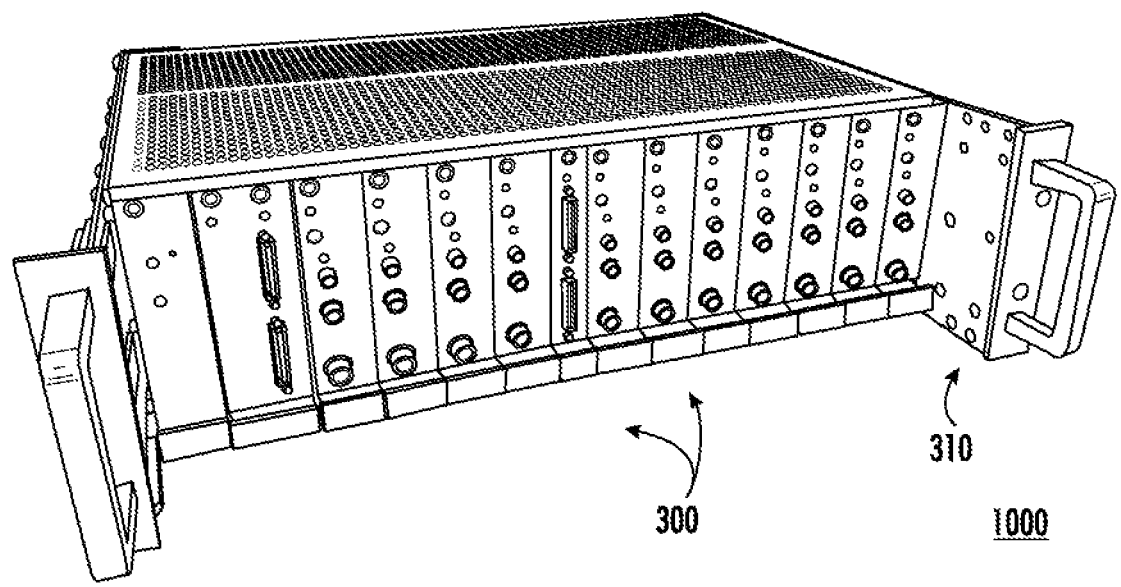
FIGS. 4C and 4D are a perspective view and front view, respectively, depicting an example embodiment of a unified diagnostics sub rack in accordance with various embodiments of the present disclosure.
Figure 4D:
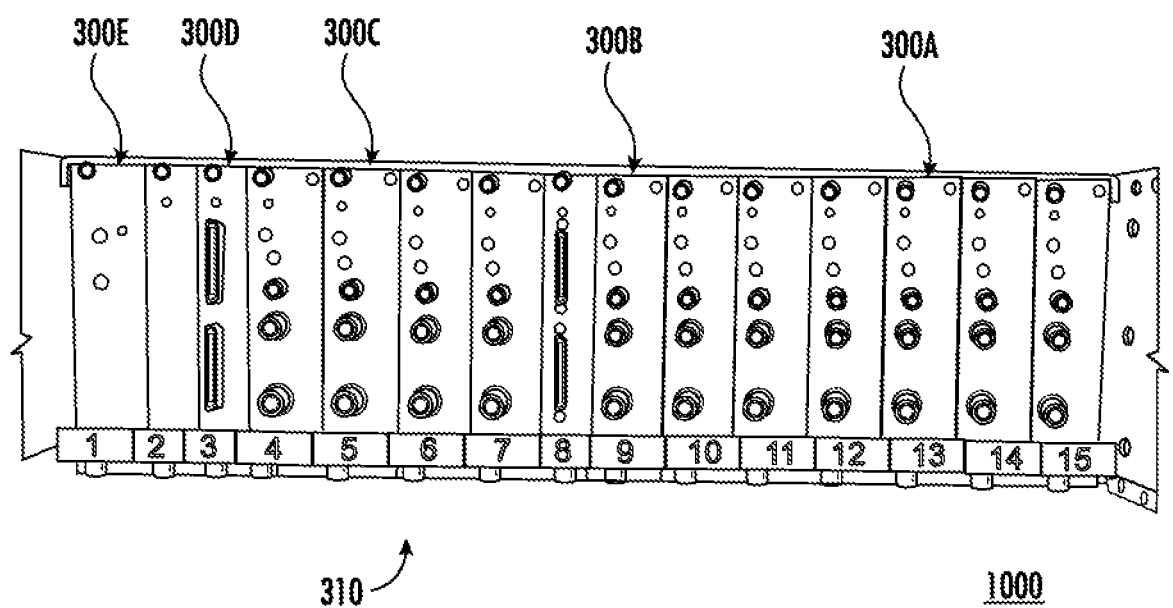

FIGS. 4C and 4D are a perspective view and front view, respectively, depicting an example embodiment of a sub rack 310 having fifteen slots 302 for housing or coupling with various modules 300.

Modules 300 are configured to be insertable into and removable from sub rack 310. This allows sub rack 310 to be configured and reconfigured as needed to operate with beam systems 10 having various and changing componentry. This further allows particular modules 300 to be removed and replaced to address a failure, or to upgrade the module electronics. The embodiments of modules described herein can include electronics 309 mounted to a printed circuit board (PCB) 301 (see FIG. 4A). Electronics 309 can be configured to perform the various diagnostics and other functions required by each application such as, e.g., measuring current, measuring voltage, measuring frequency, measuring temperature, detecting a fault, and any combination thereof.

The module embodiments can include a front panel 305 having a user interface 307 with a display, input and/or output ports (I/O ports), and/or controls for a user (see FIG. 4A). The display can include a screen and/or indicators (such as LEDs) that convey information representative of modes of operation of module 300 (e.g., ready status, fault status, offline status, etc.). The control(s) can be configured to adjust one or more settings or operating parameters of module 300. In the example embodiment depicting in FIGS. 4C-4D, the front panels of modules 300A-C (see FIGS. 5-7) include several connectors for functions such as voltage control of an internal power supply voltage (e.g., with a division ratio of 1:2, 1:10, 1:50, 1:100, 1:200, etc.), inputting power from an external power supply (EXT), and/or for inputting the signals from components 1001 to be measured (INPUT 4 CH, INPUT 2 CH, INPUT 1 CH). Modules 300A-C also include a control (ADJ) for adjusting the internal power supply.

Sub rack 310 can include a backplane 306 having one or more corresponding sockets 304A-304N. Each module 300 can include, on a side for inserting into a slot 302 of sub rack 310, a connector (e.g., having 32 pins) for plugging into or otherwise communicatively coupling with backplane 306 in order to exchange data, information, and/or power. Backplane 306 can include wiring (not shown) for routing signals to and from each of modules 300 as well as to and from a DAQ 2000 (e.g., see FIG. 2). Backplanes 306 can also be communicatively coupled with backplanes 306 of other sub racks 310, to permit communication between sub racks 310. Sub rack 310 can further include, on a rear side of sub rack 310, a power input (not shown) (e.g., 125/250 VAC) as well as fuses (e.g., 250 VAC, 2 A), and a line filter.

In an example embodiment where sub rack 310 includes multiple slots 302, the slots can be allocated among various components, which can be modular components, such as one or more diagnostics modules 300A-C (FIGS. 5-7), one or more cross connection modules 300D (FIG. 9), and one or more power supply modules 300E (FIG. 4D). Power supply module 300E can receive power from an external power supply and convert the power to another type (AC/DC conversion, DC/AC conversion) and/or regulate the voltage up or down. An example slot allocation for a sub rack 310 is depicted below in Table 1.

TABLE 1

| Slot # | Description | Comments |
|---|---|---|
| 1 | Power Supply module 300E | Can distribute power to other slots of sub rack 310 |
| 2 | Blank | Blank slot |
| 3, 8 | Cross communication module 300D | Slots 3, 8 can receive cross communication modules 300D |
| 4, 5, 6 | 4-channel module 300C | Slots 4-9 can receive any type of module 300A-C |
| 7, 9 | 2-channel module 300B | Slots 4-9 can receive any type of module 300A-C, slots 10-15 can receive single and dual channel modules 300A, 300B |
| 10, 11, 12, 13, 14, 15 | 1-channel module 300A | Slots 4-9 can receive any type of module 300A-C, slots 10-15 can receive single and dual channel modules 300A, 300B |

Figure 5:
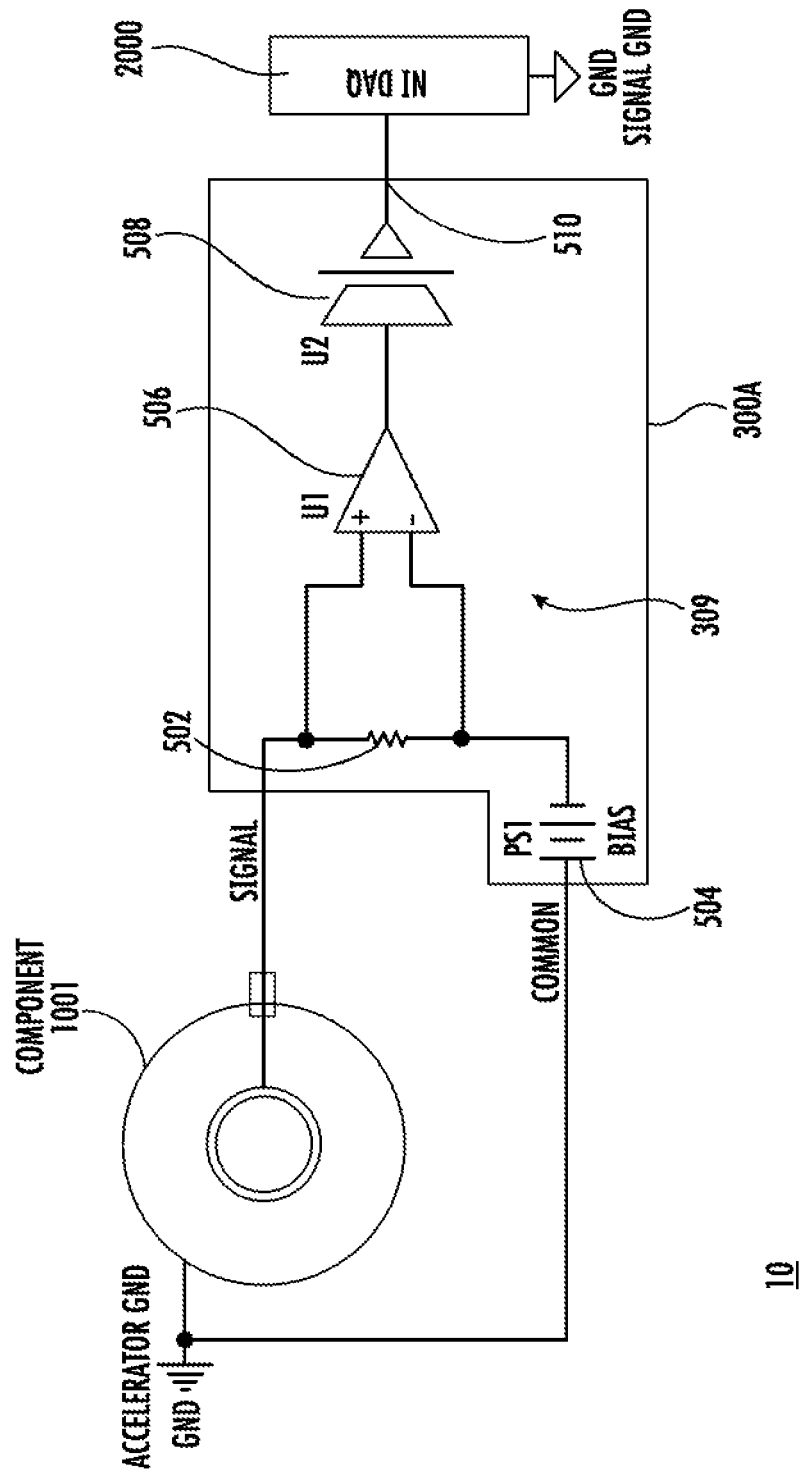
FIG. 5 illustrates a schematic of an example embodiment of a single channel module for use with embodiments of the present disclosure.

FIG. 5 illustrates a schematic of an example embodiment of a single channel module 300A for use with embodiments of the present disclosure. Electronics 309 can be configured as any type of circuitry requisite for the beam system interface. Various amplifier types can be relied upon depending on the design (e.g., voltage, trans impedance, trans conductance, and current amplifiers). In FIG. 5, single channel module 300A includes an amplifier 506 configured to obtain a measured current of component 1001 (e.g., a water-cooled aperture). In this embodiment, amplifier 506 is a differential amplifier. A differential voltage drop across a shunt resistor Rshunt 502, placed between the measured signal (e.g., Signal) from component 1001 and a power supply 504 (e.g., Common), is detected by differential amplifier 506. Isolation circuitry such as an isolating amplifier 508 can optionally provide optical isolation in order to allow for measurement of signals in the presence of a relatively higher voltage. The differential voltage drop is provided to DAQ 2000 by way of module output 510. Connections for obtaining measurements from component 1001 can include coaxial connections or twisted pair connections. The twisted pair connections can be shielded to provide for suppression of electromagnetic noise. Power supply 504 can be internal to module 300 or can be supplied externally (e.g., through UI 307).

Figure 8:
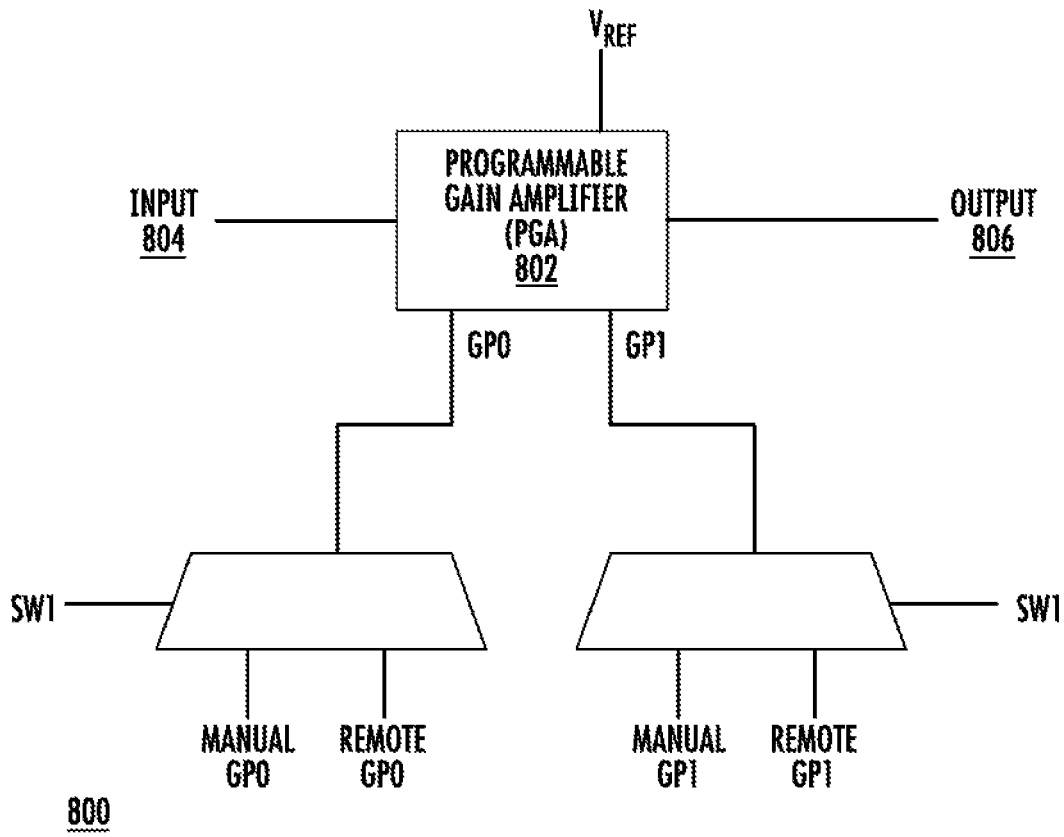
FIG. 8 illustrates a schematic of an example embodiment of programmable gain amplification for use with embodiments of the present disclosure.

In an example as shown in FIG. 5, a differential output voltage of single channel module 300 can be written according to equation (1):

$$U_{out}^{diff} = I_{in} \times R_{sh} \times G_{PGA} \times \frac{1}{3} \quad (1)$$

where $I_{in}$ is the input current, $R_{sh}$ is the shunt resistance (e.g., Rshunt in FIG. 5) (e.g., 0.1-100 k$\Omega$), and $G_{PGA}$ is the gain of the programmable gain amplifier, which is programmable to one of a different number of levels (e.g., can be switched between any number of two or more settings between 1 and 500 V/V; see, e.g., FIG. 8). That is, amplifier 506 can include or be configured to operate with a programmable gain amplifier 802 as depicted in FIG. 8 such that its gain is controllable either manually or remotely. For example, system 1000 can include a switch to alternate between manual and remote configurations for determining gain or another operating parameter of each module 300. In some embodiments, this module 300 or (a different one such as a cross-communication module) or sub rack 310 of system 1000 can include a switch that, when actuated in a first position, results in a programmable gain amplifier of single channel module 300 entering a configuration where its gain is remotely controlled by control system 3001A or computing device 3002. When in a second position, the switch can cause the module 300 to have its settings controlled manually (e.g., the switch can have multiple positions each corresponding to a particular gain).

The maximum sensing current of the example single channel module 300 can be written according to equation (2):

$$I_{in} \leq \frac{6 \text{ V}}{R_{sh}} \quad (2)$$

An example single channel module 300 can further include several switches as part of electronics 309, for example, for switching between a biased and grounded mode of operation and for switching bias polarity. Examples of bias polarities available using an example embodiment of single channel module 300 with multiple switches are shown in Table 2.

TABLE 2

| Mode | SW1 | SW2 | SW3 | SW4 |
|---|---|---|---|---|
| Positive Internal Bias | Biased | Internal | Positive | Positive |
| Negative Internal Bias | Biased | Internal | Negative | Negative |
| Positive External Bias | Biased | External | Positive | Positive |
| Negative External Bias | Biased | External | Negative | Negative |
| No Bias | Grounded | External | Positive | Negative |

Figure 6:
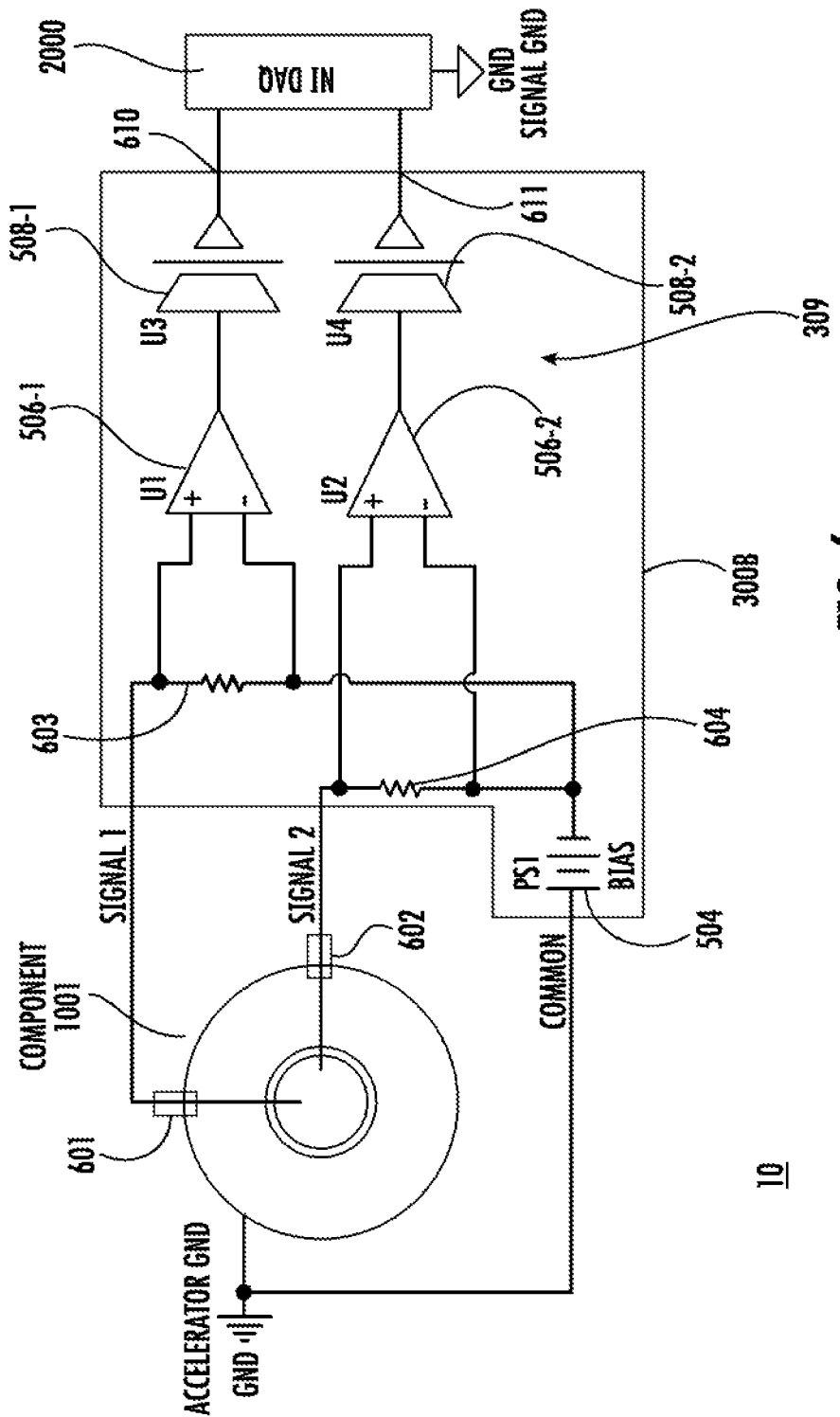
FIG. 6 illustrates a schematic of an example embodiment of a dual channel module for use with embodiments of the present disclosure.

FIG. 6 illustrates a schematic of an example embodiment of a multiple channel module 300B for use with embodiments of the present disclosure. Modules 300 can be configured to measure signals in any number of one or more channels. Here, module 300B is configured to measure, process, or otherwise act upon signals of two different channels (Signal 1 and Signal 2) connected to different elements 601, 602 (e.g., electrodes, magnets, or others) of component 1001. In FIG. 6, dual channel module 300B includes amplifiers 506-1, 506-2 configured to obtain a measured current of elements 601 and 602 of component 1001 (e.g., an XY beam profiler). In this example, amplifiers 506-1 and 506-2 are configured as differential amplifiers. A differential voltage drops across shunt resistors Rshunt 602, Rshunt 604, placed between the measured signals (e.g., Signal 1, Signal 2) from component 1001 and power supply 610 (e.g., Common), are detected by amplifiers 506-1 and 506-2. Additional amplifiers 508-1 and 508-2 (e.g., isolating amplifiers) can be included to provide optical isolation in order to allow for measurement of signals in the presence of high voltage. The differential voltage drops for each channel are provided to DAQ 2000 by way of module outputs 610 and 611. Connections for obtaining measurements from the component can include coaxial connections or twisted pair connections. The twisted pair connections can be shielded to provide for suppression of electromagnetic noise.

In an example as shown in FIG. 6, a differential output voltage of dual channel module 300 can be written according to equation (3):

$$U_{out}^{diff} = I_{in} \times R_{sh} \times G_{PGA} \times \frac{1}{3} \quad (3)$$

where $I_{in}$ is the input current, $R_{sh}$ is the shunt resistance (e.g., Rshunt 602 or Rshunt604 in FIG. 6) (e.g., 3 kΩ), and $G_{PGA}$ is the gain of the programmable gain amplifier (e.g., can be switched between any number of two or more settings between 1 and 500 V/V; see, e.g., FIG. 8). That is, differential amplifiers 606 and 608 can each include or be configured to operate with a programmable gain amplifier 802 as depicted in FIG. 8 such that its gain is controllable either manually or remotely as described with respect to FIG. 5.

The maximum sensing current of the example dual channel module 300 can be written according to equation (4):

$$I_{in} \leq \frac{6 \text{ V}}{R_{sh}} \quad (4)$$

An example dual channel module 300B can further include several switches as part of electronics 309, for example, for switching between a biased and grounded mode of operation and for switching bias polarity. Examples of bias polarities available using an example dual channel module 300B with multiple switches are shown above in Table 2.

Figure 7:
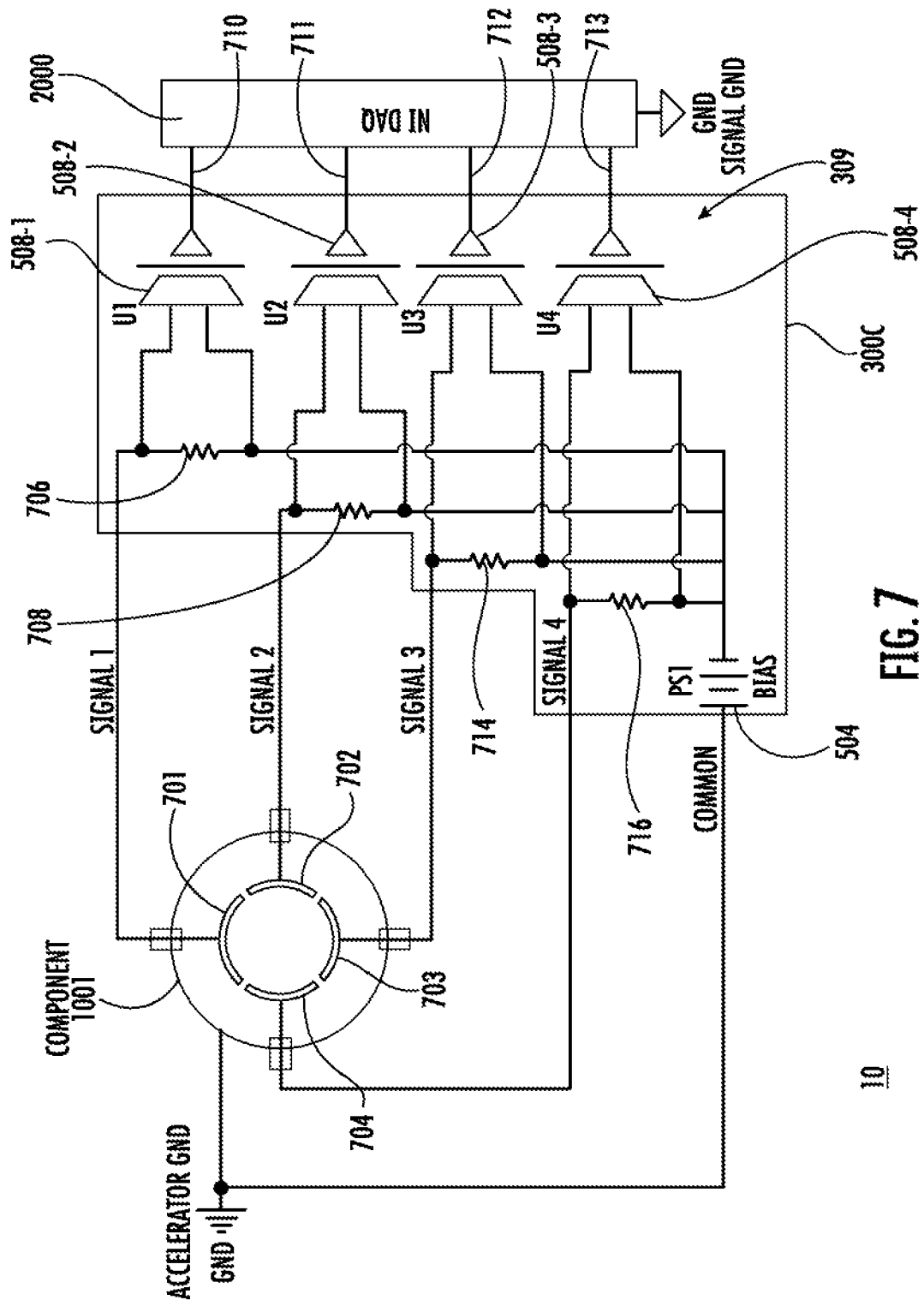
FIG. 7 illustrates a schematic of an example embodiment of a quadruple channel module for use with embodiments of the present disclosure.

FIG. 7 illustrates a schematic of an example embodiment of a quadruple channel module 300C for use with embodiments of the present disclosure. In FIG. 7, quadruple channel module 300C includes amplifiers 508-1, 508-2, 508-3, 508-4 for obtaining a measured current of elements 701, 702, 703, 704, respectively, of component 1001 (e.g., a beam position monitor). As shown in FIG. 7, differential voltage drops across shunt resistors Rshunt 702, Rshunt 704, Rshunt 714, and Rshunt 716 placed between the measured signals (e.g., Signal 1, Signal 2, Signal 3, Signal 4) from component 1001 and power supply 720 (e.g., Common), are detected by isolating amplifiers 706, 708, 710, and 712, respectively, which can optionally provide optical isolation in order to allow for measurement of signals in the presence of high voltage. The differential voltage drops for each channel are provided to DAQ 2000 by way of module outputs 710-713. No amplifiers 506 are implemented in this example, but can be in other embodiments. Connections for obtaining measurements from the component can include coaxial connections or twisted pair connections. The twisted pair connections can be shielded to provide for suppression of electromagnetic noise.

In an example as shown in FIG. 7, a differential output voltage of quadruple channel module 300C can be written according to equation (5):

$$U_{out}^{diff} = I_{in} \times R_{sh} \times \frac{1}{3} \quad (5)$$

where $I_{in}$ is the input current and $R_{sh}$ is the shunt resistance (e.g., Rshunt1, Rshunt2, Rshunt3, or Rshunt4 in FIG. 7). The maximum sensing current of the example quadruple channel module 300C can be written according to equation (6):

$$I_{in} \leq \frac{12 \text{ V}}{R_{sh}} \quad (6)$$

An example quadruple channel module 300C can further include several switches as part of electronics 309, for example, for switching between a biased and grounded mode of operation and for switching bias polarity. Examples of bias polarities available using an example quadruple channel insertable measurement board with multiple switches are shown above in Table 2.

FIG. 8 illustrates a schematic of an example embodiment of programmable gain amplification for use with embodiments of the present disclosure. In FIG. 8, programmable gain amplification circuitry 800, for inclusion in one or more modules 300 (e.g., single channel, dual channel, triple channel, quadruple channel, or cross connection, etc.) according to embodiments herein, includes a programmable gain amplifier 802 having an input 804 and an output 806. For example, input 804 can be associated with a positive terminal input (e.g., Signal in FIG. 5, Signal 1 or Signal 2 in FIG. 6). Output 806 can be associated with a measured signal delivered to isolation amplifiers (e.g., 506 in FIG. 5, or 612, 614 in FIG. 6). Vref can be associated with a common power supply (e.g., PS1 504 in FIG. 5, PS1 610 in FIG. 6).

Output 806 of the programmable gain amplifier 802 is the input 804 multiplied or amplified by a selected gain G. That is, Output 806=G*Input 804. The gain G of programmable gain amplifier 802 can be set to one of any number of predetermined discrete levels, or can be variable (analog). In one example embodiment, the gain G can be set according to bits GP0 and GP1, with example values in Table 3 below. In other embodiments, gain settings can be set to any desired value, e.g., between 1 and 500.

Gain selection bits GP0 and GP1 can be controlled using a switch in electronics 309 (or elsewhere) or remotely by way of control system 3001A (FIG. 2) as described herein. Enabling of manual or remote control of the gain selection bits GP0 and GP1 can be accomplished by way of a switch SW1 such that when the switch SW1 is in a first position (e.g., set to manual selection), GP0 and GP1 are set according to settings (e.g., Manual GP0, Manual GP1) of a manual switch (not shown) of the programmable gain amplification circuitry 800 or module 300. By way of further example, when the switch SW1 is in a second position (e.g., set to remote selection), GP0 and GP1 are set according to settings (e.g., Remote GP0, Remote GP1) provided by way of a control system 3001A and/or a computing device 3002 (FIG. 2).

TABLE 3

| Gain multiplier | GP1 | GP0 |
| --- | --- | --- |
| 1 | 0 | 0 |
| 10 | 0 | 1 |
| 100 | 1 | 0 |
| Forbidden state | 1 | 1 |

One or more components as depicted in FIG. 8 can be split across multiple modules 300 for use with embodiments of the present disclosure. For example, one or more programmable gain amplifiers can be included in a module 300A, B,C while the manual switch (not shown) and/or switch SW1 can be included in a cross connection communication module 300D.

Figure 9:
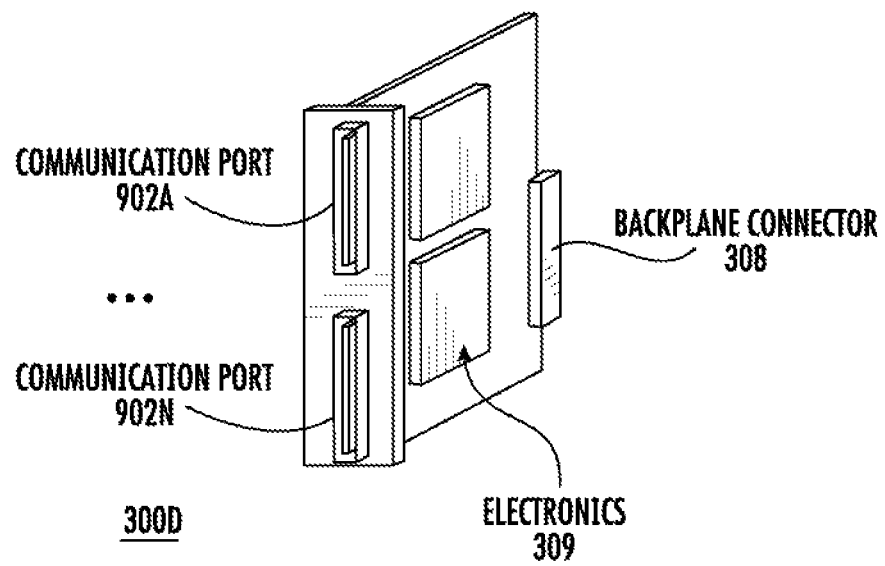
FIG. 9 illustrates an example embodiment of a cross connection module for use with embodiments of the present disclosure.

FIG. 9 illustrates an example embodiment of a cross connection communication module 300D according to various embodiments of the present disclosure. Cross connection module 300D is configured to route signals from any number of one or more sources (e.g., other modules 300A-D) input to cross connection module 300D at one or more first ports, to any number of one or more second ports for outputting to one or more sinks or destinations (e.g., DAQ 2000). In some embodiments cross communication module 300D performs the routing without modifying the signal (e.g., a hardwired connection only with no amplification). Cross connection module 300D can be unidirectional (only routing data from one port to another, and not in the opposite direction) or bidirectional (routing data back and forth between ports). Cross connection module 300D can have the signal paths hardwired such that the paths do not change (e.g., information input to a first pin of a first port is hardwired to a second pin of a second port), or cross connection module 300D can be configured to set and modify signal paths, so that information routing can be changed (e.g., information input to a first pin of a first port can be routed to either a second pin of a second port or a third pin of the second port (or of a different port)).

In FIG. 9, example cross connection module 300D can include one or more communication ports 902A-902N for routing measured signals received by way of a backplane connector 904 to DAQ 2000 (FIG. 2) or another device. An example cross connection module 300D can further include circuitry as part of electronics 309 for routing multiple subsets of signals, each subset associated with a dedicated communication port of the one or more communication ports 902A-902N.

For example, a communication port, 902A, can have capability to route multiple (e.g., 2, 4, 8, 16, 32, 64, 128, etc.) channels of signals such that signals from multiple modules 300A-D plugged into a same or different sub rack 310 as cross connection module 300D can be routed into cross connection module 300D via backplane connector 308 and then output from module 300D through communication port 902A, and from there to DAQ 2000 or another device. That is, any combination of modules 300A-D (e.g., single, dual, triple, quadruple channel, or otherwise) can be housed in one or more sub racks 310 and the signals from those modules 300A-D can be routed using backplane 306 to cross connection module 300D (of the same or a different sub rack 310) in order to be routed through the communication port 902A to DAQ 2000 or another device.

Further, communication port 902N can have capability to route multiple channels of signals (which can be the same or different signals being routed to any other port, e.g., 902A) such that signals from multiple modules 300A-D plugged into sub rack 310 (either the same or different as cross connection module 300) can be routed through communication port 902N to DAQ 2000 or another device. That is, any combination of modules 300 can be housed in a sub rack 310 and the signals from those modules 300 can be routed using backplane 306 to a cross connection module 300D in order to be routed through the communication port 902N to the digital acquisition system.

In example embodiments, communication ports 902A-902N are configured for connection to DAQ 2000 by way of SCSI (e.g., small computer system interface) cables (not shown). Other connections suitable for use with communication ports 902A-902N are within the scope of the present disclosure.

The ports 902A-N can each have multiple line contacts (e.g., pins, leads) where each line can carry a signal dedicated to a particular source or sink. For example, each port can have dedicated lines for each of, e.g., single channel output 510 from one or modules 300A, dual channel outputs 610 and 611 from one or more modules 300B, and quad channel outputs 710-713 from one or more quad channel modules 300C. Cross communication module 300D can also be configured to output: identification information that identifies the type of each module 300 in a particular slot 302 (e.g., a predetermined code corresponding to each module type (e.g., single, dual, triple, quad, cross communication, power, etc.); gain identification information that specifies the gain setting for each module 300 (and whether that gain value is remote or manually determined); and status information such as whether a particular module is ready for use and the polarity of the bias voltage applied to a detector, as detailed in the example of Table 4 below.

TABLE 4

| Status | Pin 1 for slot X | Pin 2 for slot X |
| --- | --- | --- |
| The module in slot X is ready with the positive bias voltage applied to a detector. | 1 | 0 |
| The module in slot X is ready with the negative bias voltage applied to a detector. | 0 | 1 |
| The module in slot X is ready with NO bias applied to a detector | 1 | 1 |
| The module is slot X is not ready. | 0 | 0 |

One or more sub racks 310 of example embodiments can house, at any given time, any combination of types of modules 300, such as one or more cross connection modules, single channel insertable measurement boards, dual channel insertable measurement boards, quadruple channel insertable measurement boards, power supply modules, or other insertable boards. Further, one or more sub racks 310 can have one or more slots 302 left empty as desired.

In example embodiments, each cross connection module 300D can include one or more switches (not shown) for setting a separate gain multiplier for different sets of modules. For example, a separate gain multiplier can be set using one or more switches (not shown) of the cross connection module 300D for a first set of modules 300 associated with a first communication port (e.g., 902A) while another separate gain multiple can be set using one or more switches (not shown) of the cross connection module 300D for a second set of modules 300 associated with a second communication port (e.g., 902N).

Through the use of the present diagnostics modules 300A-C as well as cross connection modules 300D, embodiments of the present disclosure provide a unified diagnostics system whereby the need is eliminated for intermediate wiring, signal conditioning, or other filtering in order to obtain measurements from disparate beam system components at a central digital acquisition system. Further, while conventional systems for obtaining such measurements can require synchronization based on various beam parameters and beam system operation modes, the present disclosure eliminates such synchronization requirements. Although modules 300A-C are described primarily as performing diagnostics including the taking of current measurements, other types of measurements can be made (e.g., voltage, frequency, phase, temperature) with electronics 309 configured for the collection of those other types of measurements. Further, the modules 300 can be configured to apply a stimulus (e.g., current or voltage) as part of the diagnostics function.

The embodiments described herein are not limited to use in only the specific applications set forth, and can also be used in beam systems implemented in industrial or manufacturing applications, such as the manufacturing of semiconductor chips, the alteration of material properties (such as surface treatment) of a work piece, the irradiation of food, and pathogen destruction in medical sterilization. The embodiments can further be used in imaging applications, such as cargo or container inspection. By way of another non-exhaustive example, the embodiments can be used in particle accelerators for medical applications, such as medical diagnostic systems, medical imaging systems, or other non-BNCT radiation therapy systems.

As will be appreciated, any such computer program instructions and/or other type of code can be loaded onto a computer, processor, or other programmable apparatus' circuitry to produce a machine, such that the computer, processor, or other programmable circuitry that executes the code on the machine creates the means for implementing various functions, including those described herein.

As described above and as will be appreciated based on this disclosure, embodiments of the present disclosure can be configured as systems, methods, mobile devices, backend network devices, and the like. Accordingly, embodiments can include various structures including entirely of hardware or any combination of software and hardware. Furthermore, embodiments can take the form of a computer program product on at least one non-transitory computer-readable storage medium having computer-readable program instructions (e.g., computer software) embodied in the storage medium. Any suitable computer-readable storage medium can be utilized including non-transitory hard disks, CD-ROMs, flash memory, optical storage devices, or magnetic storage devices.

Processing circuitry for use with embodiments of the present disclosure can include one or more processors, microprocessors, controllers, and/or microcontrollers, each of which can be a discrete chip or distributed amongst (and a portion of) a number of different chips. Processing circuitry for use with embodiments of the present disclosure can include a digital signal processor, which can be implemented in hardware and/or software of the processing circuitry for use with embodiments of the present disclosure. Processing circuitry for use with embodiments of the present disclosure can be communicatively coupled with the other components of the figures herein. Processing circuitry for use with embodiments of the present disclosure can execute software instructions stored on memory that cause the processing circuitry to take a host of different actions and control the other components in figures herein.

Memory for use with embodiments of the present disclosure can be shared by one or more of the various functional units, or can be distributed amongst two or more of them (e.g., as separate memories present within different chips). Memory can also be a separate chip of its own. Memory can be non-transitory, and can be volatile (e.g., RAM, etc.) and/or non-volatile memory (e.g., ROM, flash memory, F-RAM, etc.).

Computer program instructions for carrying out operations in accordance with the described subject matter can be written in any combination of one or more programming languages, including an object oriented programming language such as Java, JavaScript, Smalltalk, C++, C #, Transact-SQL, XML, PHP or the like and conventional procedural programming languages, such as the "C" programming language or similar programming languages.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In some embodiments, a modular diagnostics interface system includes a rack having a backplane and one or more insertable modules each configured to communicably couple with the backplane of the rack. In some of these embodiments, at least one of the one or more modules is configured to collect a measured current from a component of a beam system.

In some of these embodiments, the one or more inserter modules include at least one cross communication module configured to route a signal from a first port to a second port.

In some of these embodiments, the rack includes multiple slots. In some of these embodiments, each slot is configured to receive an insertable module.

In some of these embodiments, the backplane routes signals from the one or more insertable modules to the at least one cross communication module.

In some of these embodiments, at least one of the one or more insertable modules is a single channel measurement board.

In some of these embodiments, the single channel measurement board includes a differential amplifier for measuring a differential voltage drop experienced across a shunt resistor electrically coupled between a first power supply and a measured signal from a component of a beam system.

In some of these embodiments, at least one of the one or more insertable modules is a multiple channel measurement board.

In some of these embodiments, the multiple channel measurement board includes multiple differential amplifiers for measuring multiple differential voltage drops experienced across multiple shunt resistors each electrically coupled between a first power supply and a measured signal of multiple measured signals from a component of a beam system.

In some of these embodiments, the multiple channel measurement board includes one of two or four channels.

In some of these embodiments, at least one of the one or more insertable modules includes one or more programmable gain amplifiers. In some of these embodiments, the one or more programmable gain amplifiers are manually controllable or remotely controllable. In some of these embodiments, a cross connection module includes one or more switches configured to set manual or remote control of the one or more programmable gain amplifiers.

In some of these embodiments, a programmable gain amplifier is configured to operate with one of multiple gain settings.

In some of these embodiments, the multiple gain settings comprise at least two values between 1 V/V and 500 V/V.

In some of these embodiments, the component of the beam system includes one or more of a beam position monitor, an aperture, a water cooled aperture, a faraday cup, an XY beam profiler, or a beam dump.

In some of these embodiments, at least one of the one or more insertable modules is configured to be biased using a biasing voltage of one of positive or negative polarity.

In some of these embodiments, at least one of the one or more insertable modules is configured to be biased using a biasing voltage serving as one of a current source or a current sink for the measured current.

In some of these embodiments, the modular diagnostics interface system is configured for external biasing based on an external biasing power supply. In some of these embodiments, the external biasing power supply provides a range of voltage of up to 1000 V.

In some of these embodiments, the collected measured current from the component of the beam system is provided to a digital acquisition system with one or more of galvanic isolation to prevent ground loops or shielding to reduce electromagnetic noise.

In some of these embodiments, at least one of the one or more insertable modules includes a front panel having a user interface. In some of these embodiments, the user interface includes at least one indicator and at least one port.

In some of these embodiments, the rack is a sub rack of a multi-shelf rack.

In some embodiments, a beam system includes a modular diagnostics interface system according to any of the foregoing embodiments positioned along the beam system. In some of these embodiments, the beam system further a digital acquisition system communicably coupled to the modular diagnostics interface system. In some of these embodiments, a control system configured to receive one or more signals from the digital acquisition system.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments can be recited in or added to the claims, as well as negative limitations that define the inventive scope of the claims by features, functions, steps, or elements that are not within that scope.

What is claimed is:

1. A modular diagnostics interface system, comprising:
a rack comprising a backplane; and
one or more insertable modules, each insertable module configured to communicably couple with the backplane of the rack and comprising at least one cross communication module configured to route a signal from a first communication port to a second communication port, wherein at least one insertable module of the one or more insertable modules is configured to collect a measured current from a component of a beam system when the at least one insertable module is communicably coupled with the component.

2. The modular diagnostics interface system of claim 1, wherein the rack comprises a plurality of slots, wherein each slot of the plurality of slots is configured to receive an insertable module of the one or more insertable modules.

3. The modular diagnostics interface system of claim 1, wherein the backplane routes signals from the one or more insertable modules to the at least one cross communication module.

4. The modular diagnostics interface system of claim 1, wherein at least one of the one or more insertable modules is a single channel measurement board.

5. The modular diagnostics interface system of claim 4, wherein the single channel measurement board comprises a shunt resistor, a first power supply, and a differential amplifier for measuring a differential voltage drop experienced across the shunt resistor electrically coupled between the first power supply and a measured signal from the component of the beam system.

6. The modular diagnostics interface system of claim 1, wherein at least one of the one or more insertable modules is a multiple channel measurement board.

7. The modular diagnostics interface system of claim 6, wherein the multiple channel measurement board comprises a plurality of shunt resistors, a first power supply, and a plurality of differential amplifiers for measuring a plurality of differential voltage drops experienced across the plurality of shunt resistors, wherein each shunt resistor of the plurality of shunt resistors is electrically coupled between the first power supply and a measured signal of a plurality of measured signals from the component of the beam system.

8. The modular diagnostics interface system of claim 6, wherein the multiple channel measurement board comprises one of two or four channels.

9. The modular diagnostics interface system of claim 1, wherein at least one of the one or more insertable modules comprises one or more programmable gain amplifiers.

10. The modular diagnostics interface system of claim 9, wherein the one or more programmable gain amplifiers are manually controllable or remotely controllable.

11. The modular diagnostics interface system of claim 10, further comprising one or more additional cross connection modules, wherein a cross connection module of the one or more additional cross connection modules comprises one or more switches configured to set manual control or remote control of the one or more programmable gain amplifiers.

12. The modular diagnostics interface system of claim 9, wherein a programmable gain amplifier of the one or more programmable gain amplifiers is configured to operate with one of a plurality of gain settings.

13. The modular diagnostics interface system of claim 12, wherein the plurality of gain settings comprise at least two values between 1 V/V and 500 V/V.

14. The modular diagnostics interface system of claim 1, wherein the component of the beam system comprises one or more of a beam position monitor, an aperture, a water cooled aperture, a faraday cup, an XY beam profiler, or a beam dump.

15. The modular diagnostics interface system of claim 1, wherein at least one of the one or more insertable modules is configured to be biased using a biasing voltage of one of positive polarity or negative polarity.

16. The modular diagnostics interface system of claim 1, wherein at least one of the one or more insertable modules is configured to be biased using a biasing voltage serving as one of a current source or a current sink for the measured current.

17. The modular diagnostics interface system of claim 1, wherein an insertable module of the one or more insertable modules comprises a power supply module configured for an external biasing based on an external biasing power supply that is external to the rack.

18. The modular diagnostics interface system of claim 17, wherein the external biasing power supply provides a range of voltage of up to 1000 V.

19. The modular diagnostics interface system of claim 1, further comprising communications circuitry configured to provide the collected measured current collected from the component of the beam system to a digital acquisition system.

20. The modular diagnostics interface system of claim 19, wherein the digital acquisition system is external to the rack.

21. The modular diagnostics interface system of claim 1, wherein at least one of the one or more insertable modules comprises a front panel having a user interface.

22. The modular diagnostics interface system of claim 21, wherein the user interface comprises at least one indicator and at least one port.

23. The modular diagnostics interface system of claim 1, further comprising a multi-shelf rack, and wherein the rack is a sub rack of the multi-shelf rack.

24. The modular diagnostics interface system of claim 1, further comprising one or more connections comprising one or more of galvanic isolations to prevent ground loops or shielding to reduce an electromagnetic noise, wherein the measured current collected from the component of the beam system is provided to a digital acquisition system via the one or more connections.

25. The modular diagnostics interface system of claim 1, further comprising:
the component of the beam system.

26. A beam system, comprising:
the modular diagnostics interface system according to claim 1 positioned along the beam system;
a digital acquisition system communicably coupled to the modular diagnostics interface system; and
a control system configured to receive one or more signals from the digital acquisition system.

* * * * *

UNITED STATES PATENT AND TRADEMARK OFFICE
CERTIFICATE OF CORRECTION

| | |
|---|---|
| PATENT NO. | : 12,083,361 B2 |
| APPLICATION NO. | : 17/411832 |
| DATED | : September 10, 2024 |
| INVENTOR(S) | : Pirogov et al. |

Page 1 of 1

It is certified that error appears in the above-identified patent and that said Letters Patent is hereby corrected as shown below:

In the Claims

<u>Column 20,</u>
Line 16, Claim 19, "the collected measured" should read --the measured--.

Signed and Sealed this
Nineteenth Day of August, 2025

Coke Morgan Stewart
*Acting Director of the United States Patent and Trademark Office*